US009841391B2

(12) United States Patent
Guinan et al.

(10) Patent No.: US 9,841,391 B2
(45) Date of Patent: Dec. 12, 2017

(54) HAND-HELD TEST METER WITH INTEGRATED THERMAL CHANNEL

(71) Applicant: LifeScan Scotland Limited, Inverness (GB)

(72) Inventors: Eamon Guinan, Inverness (GB); Jonathan Nelson, Inverness (GB); David Elder, Inverness (GB)

(73) Assignee: LifeSan Scotland Limited, Inverness (GB)

( * ) Notice: Subject to any disclaimer, the term of this patent is extended or adjusted under 35 U.S.C. 154(b) by 573 days.

(21) Appl. No.: 14/480,939

(22) Filed: Sep. 9, 2014

(65) Prior Publication Data
US 2016/0069828 A1 Mar. 10, 2016

(51) Int. Cl.
G01K 17/00 (2006.01)
G01N 25/18 (2006.01)
G01N 33/49 (2006.01)
G01N 33/487 (2006.01)
G01K 7/42 (2006.01)

(52) U.S. Cl.
CPC ............ G01N 25/18 (2013.01); G01K 7/427 (2013.01); G01N 33/48785 (2013.01); G01N 33/49 (2013.01)

(58) Field of Classification Search
None
See application file for complete search history.

(56) References Cited

U.S. PATENT DOCUMENTS 5,667,653 A * 9/1997 Schneider .......... G01N 27/4045
                                                204/400
2005/0045855 A1 * 3/2005 Tonapi ..................... C09K 5/14
                                                252/500

(Continued)

FOREIGN PATENT DOCUMENTS

WO         2010048294 A1    4/2010

OTHER PUBLICATIONS

International Search Report and Written Opinion issued in corresponding International Patent Application No. PCT/EP2015/070518, dated Nov. 9, 2015, 11 pages.

(Continued)

Primary Examiner — Erica Lin

(57) ABSTRACT

A hand-held test meter includes an electrically and thermally insulating case ("ETIC") with an outwardly facing surface, a test meter electrical component ("TMEC") with a thermal contact portion disposed within the electrically-insulating case, and at least one thermal channel. The thermal channel includes a proximal contact portion with a proximal contact surface, a distal contact portion with a distal surface, and a channel portion connecting the proximal contact portion and the distal contact portion. The thermal channel is integrated with the ETIC such that the thermal channel extends through the ETIC from the outwardly facing surface and to the thermal contact portion of the TMEC. The extension is such that the proximal contact surface of the thermal channel is outside of the ETIC and the distal surface of the thermal channel is in contact with the thermal contact portion of the TMEC. The thermal channel is thermally conductive and electrically-insulating.

13 Claims, 10 Drawing Sheets

(56) References Cited

U.S. PATENT DOCUMENTS

2008/0251908 A1* 10/2008 Yang ................... H01L 23/13
 257/690
2010/0128754 A1* 5/2010 Jetter ................ A61B 5/14532
 374/110
2012/0076171 A1 3/2012 Mu
2013/0279539 A1 10/2013 Matsumura et al.
2015/0177175 A1* 6/2015 Elder ................ G01N 27/3272
 205/792

OTHER PUBLICATIONS

Zhang, G. et al. "A Percolation Model of Thermal Conductivity for Filled Polymer Composites," Journal of Composite Materials, 2010 44: 963 originally published online Oct. 6, 2009, DOI: 10.1177/0021998309349690, http://jcm.sagepub.com/content/44/8/963.

* cited by examiner

HAND-HELD TEST METER WITH INTEGRATED THERMAL CHANNEL

BACKGROUND OF THE INVENTION

Field of the Invention

The present invention relates, in general, to electronic devices and, in particular, to hand-held test meters and associated methods.

Description of Related Art

The determination (e.g., detection and/or concentration measurement) of an analyte in, or a characteristic of, a fluid sample is of particular interest in the medical field. For example, it can be desirable to determine glucose, ketone bodies, cholesterol, lipoproteins, triglycerides, acetaminophen, hematocrit and/or HbA1c concentrations in a sample of a bodily fluid such as urine, blood, plasma or interstitial fluid. Such determinations can be achieved using a hand-held test meter and associated analytical test strips that employ, for example, visual, photometric or electrochemical determination techniques. Such hand-held test meters include various electrical components such as temperature sensors and micro-controllers.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention, in which.

DETAILED DESCRIPTION OF ILLUSTRATIVE EMBODIMENTS

Figure 1:
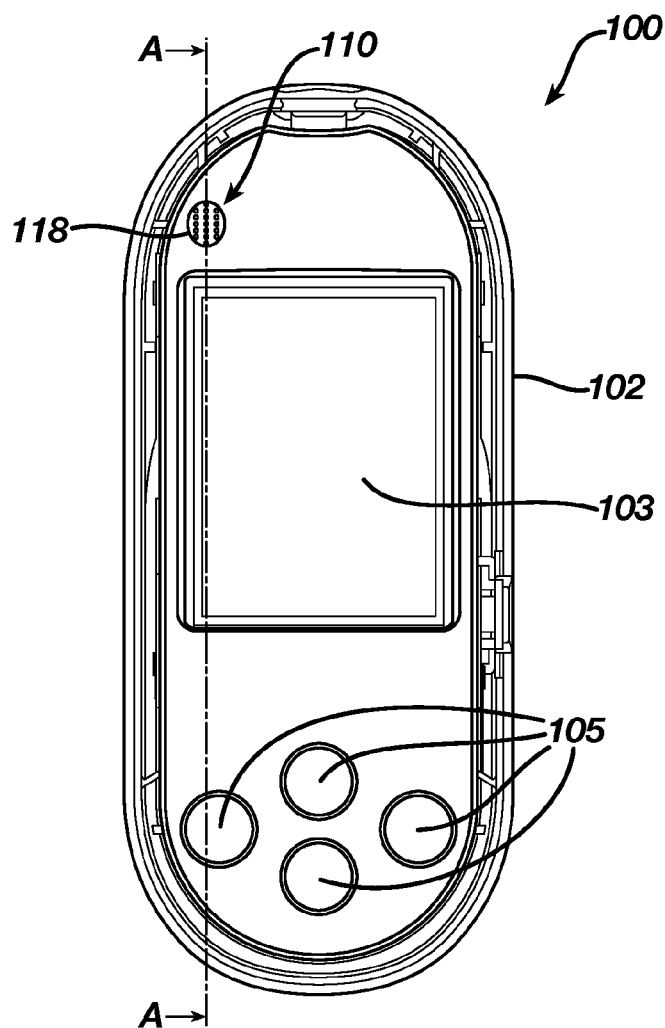
FIG. 1 is a simplified top view of a hand-held test meter according to an embodiment of the present invention.

The following detailed description should be read with reference to the drawings, in which like elements in different drawings are identically numbered. The drawings, which are not necessarily to scale, depict exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows a component part or collection of components to function for its intended purpose as described herein. As used herein, the terms "case" and "casing" refer to an outer covering or housing.

Hand-held test meters according to embodiments of the present invention (such as hand-held test meters configured for the determination of an analyte in a bodily fluid sample) include an electrically and thermally insulating case with an outwardly facing surface, a test meter electrical component (for example, a temperature sensor or a micro-controller) with a thermal contact portion disposed within the electrically and thermally insulating case, and at least one thermal channel.

The thermal channel includes a proximal contact portion with a proximal contact surface, a distal contact portion with a distal surface, and a channel portion connecting the proximal contact portion and the distal contact portion. The thermal channel is integrated with the electrically and thermally insulating case such that the thermal channel extends through the electrically and thermally insulating case from the outwardly facing surface and to the thermal contact portion of the test meter electrical component. The extension is such that the proximal contact surface of the thermal channel is outside of the electrically and thermally insulating plastic case and the distal surface of the thermal channel is in contact with the thermal contact portion of the test meter electrical component. In addition, the thermal channel is thermally conductive and electrically-insulating.

Test meters according to embodiments of the present invention are beneficial in that, for example, the thermal channel can be configured to directly transfer environmental heat to a temperature sensor within the electrically and thermally insulating case. In such a hand-held test meter, the accuracy and response time of the thermal sensor are improved. For example, if the conventional thermal response time (i.e., the time for a thermal sensor within the hand-held test meter to be operably equilibrated with a given changed environmental temperature) for a hand-held test meter is 30 minutes, hand-held test meters according to embodiments of the present invention have a significantly reduced response time of, for example, less than 15 minutes. The thermal channel can also be configured to directly transfer heat from relatively high power, heat generating electrical component(s) (e.g., a micro-controller, liquid crystal display (LCD), and USB component) disposed within the electrically and thermally insulating case to the environment, thus preventing a deleterious build-up of heat within the case.

Figure 2:
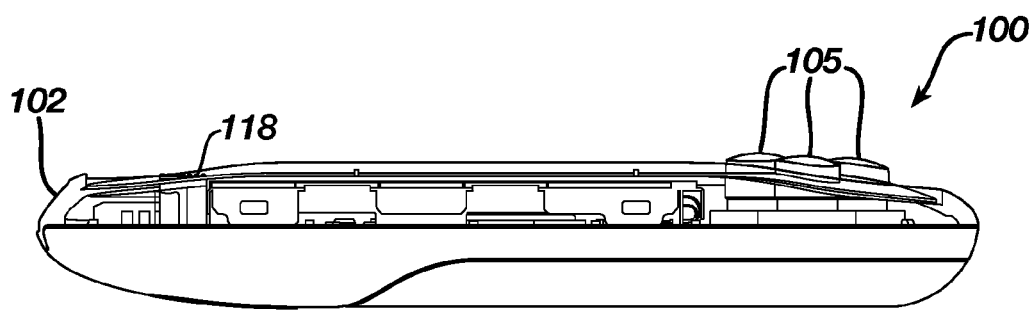
FIG. 2 is a simplified side view of the hand-held test meter of FIG. 1.
Figure 3:
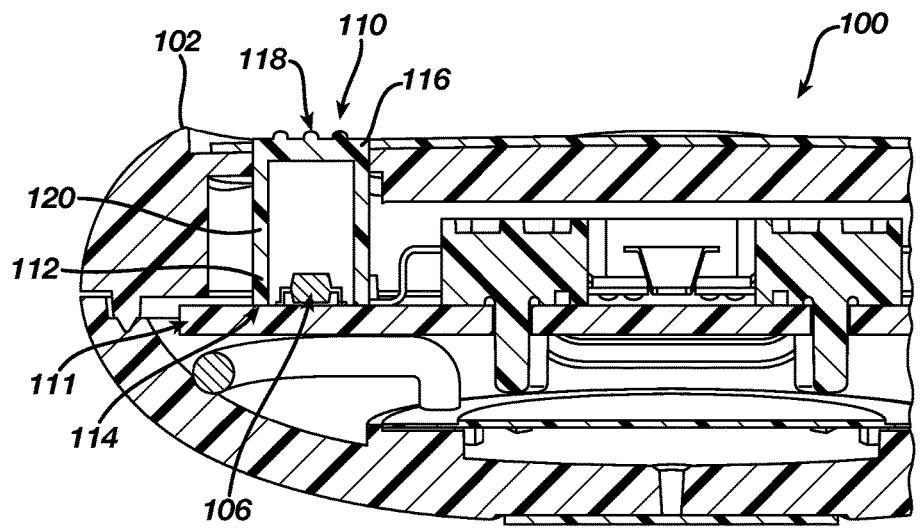
FIG. 3 is a simplified cross-sectional view of a portion of the hand-held test meter of FIG. 1 taken along line A-A of FIG. 1.
Figure 4:
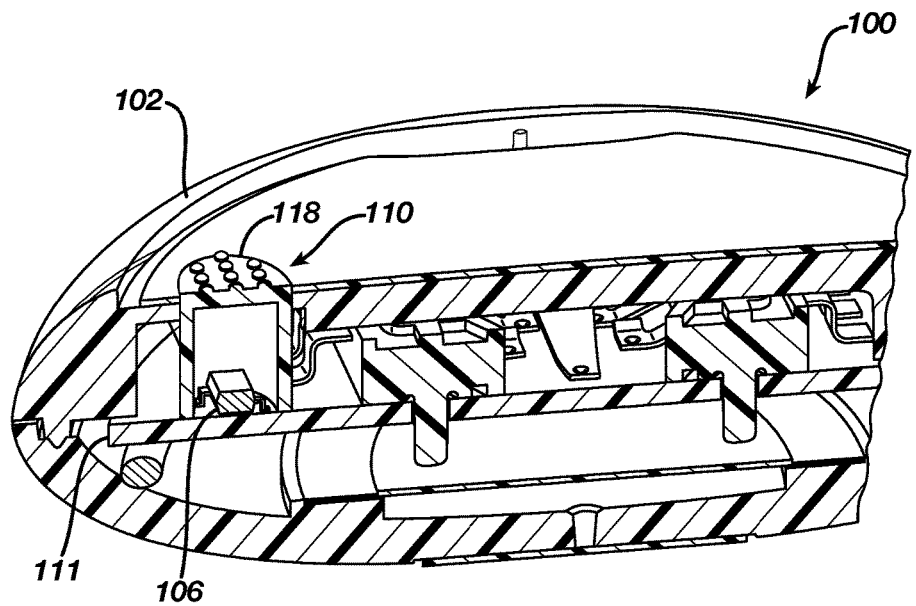
FIG. 4 is a simplified cross-sectional (also along line A-A of FIG. 1) perspective view of the hand-held test meter of FIG. 1.

FIG. 1 is a simplified top view of a hand-held test meter 100 according to an embodiment of the present invention. FIG. 2 is a simplified side view of the hand-held test meter 100. FIG. 3 is a simplified cross-sectional view of a portion of the hand-held test meter 100 taken along line A-A of FIG. 1. FIG. 4 is a simplified cross-sectional (along line A-A of FIG. 1) perspective view of hand-held test meter 100.

Figure 5A:
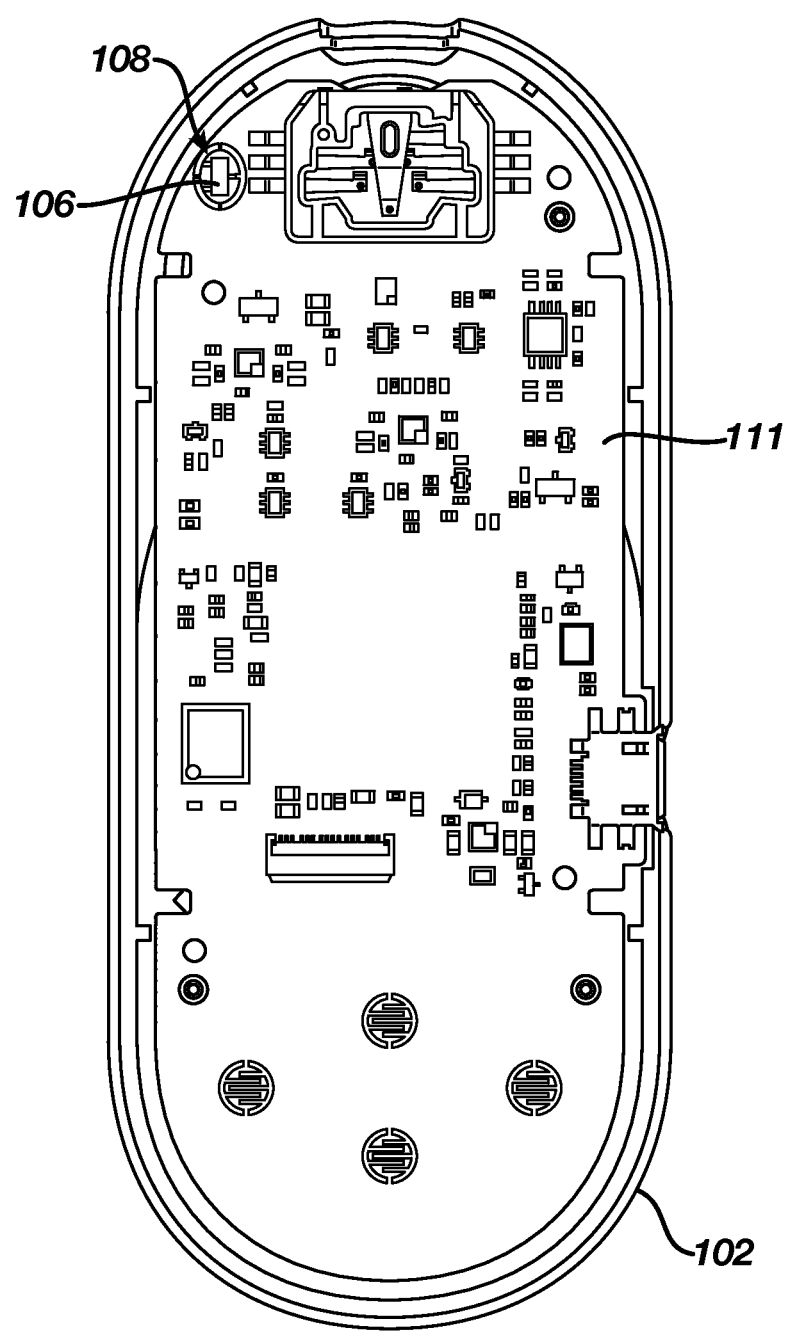
FIG. 5A is a simplified top view of the hand-held test meter of FIG. 1 dismantled to clearly depict a printed circuit board (PCB) within a casing of the hand-held test meter.
Figure 5B:
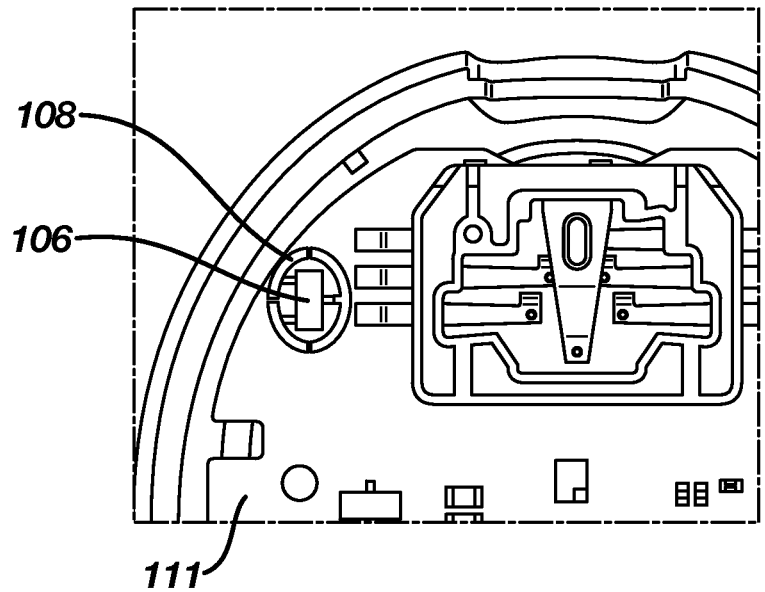
FIG. 5B is a portion of the simplified top view of FIG. 5A.
Figure 5C:
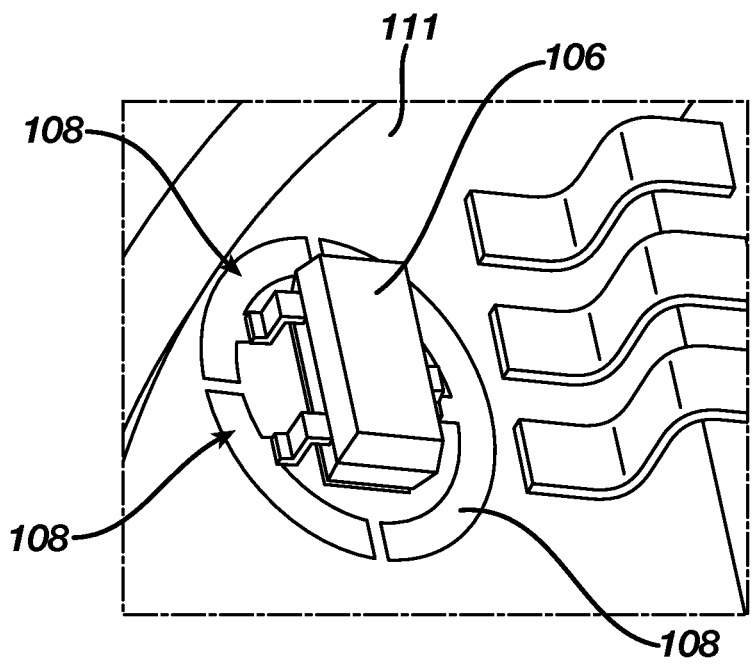
FIG. 5C is a simplified perspective depiction of a portion of the hand-held test meter of FIG. 1 as dismantled in FIGS. 5A and 5B.
Figure 6A:
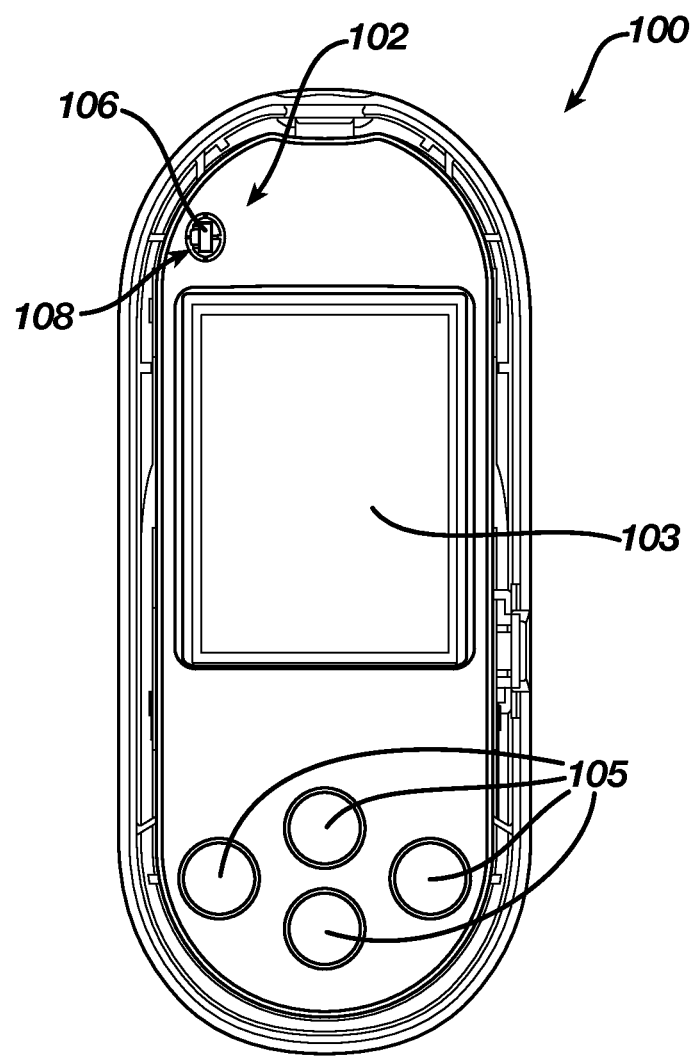
FIG. 6A is a simplified top view of the hand-held test meter of FIG. 1 in the absence of an integrated thermal channel.
Figure 6B:
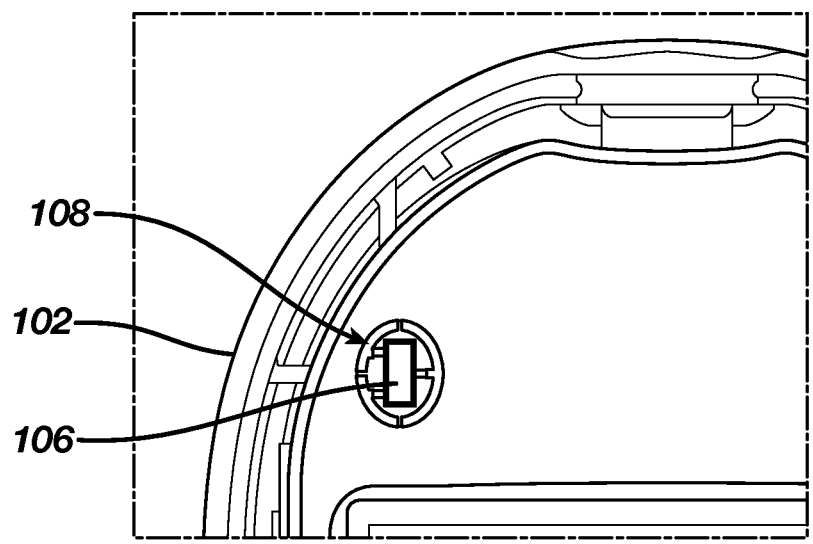
FIG. 6B is a simplified top view of a portion of the hand-held test meter of FIG. 1 in the absence of an integrated thermal channel.
Figure 6C:
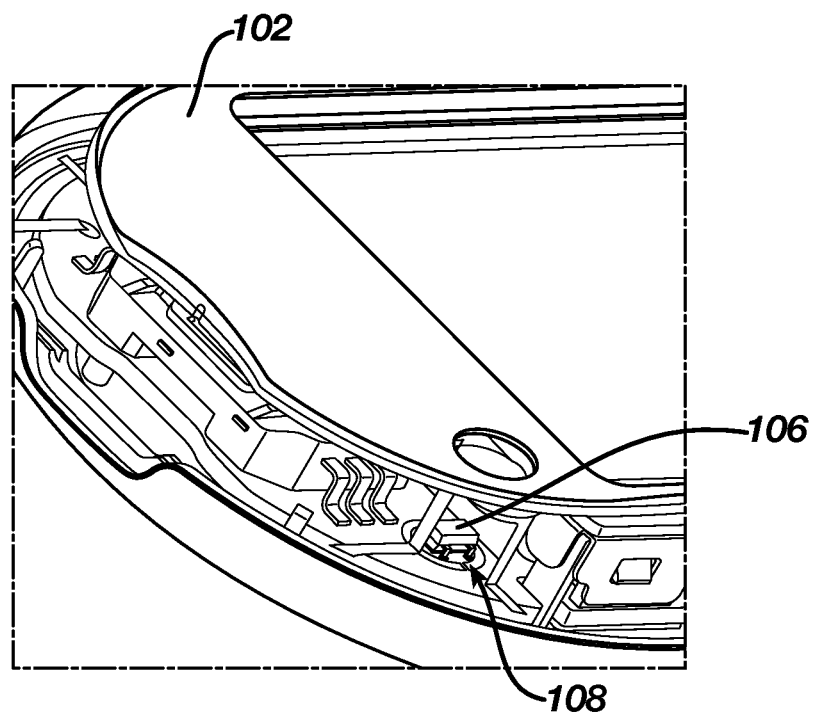
FIG. 6C is a simplified perspective view of a portion of the hand-held test meter of FIG. 1 in the absence of an integrated thermal channel.

FIG. 5A is a simplified top view of hand-held test meter 100 in a dismantled state (i.e., some components are not shown) to clearly depict a printed circuit board (PCB) within a casing of hand-held test meter 100. FIG. 5B is a portion of the simplified top view of hand-held test meter 100 of FIG. 5A. FIG. 5C is a simplified perspective depiction of a portion of hand-held test meter 100 as dismantled in FIGS. 5A and 5B. FIG. 6A is a simplified top view of the hand-held test meter of FIG. 1 in the absence of an integrated thermal channel. FIG. 6B is a simplified top view of a portion of the hand-held test meter of FIG. 1 in the absence of an integrated thermal channel. FIG. 6C is a simplified perspective view of a portion of the hand-held test meter of FIG. 1 in the absence of an integrated thermal channel.

Figure 7A:
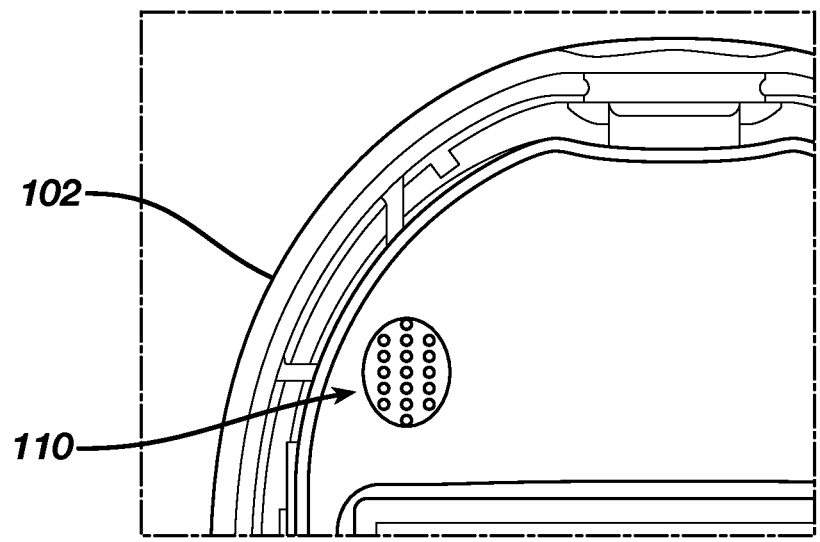
FIG. 7A is a simplified top view of a portion of the hand-held test meter of FIG. 1 including an integrated thermal channel thereof.
Figure 7B:
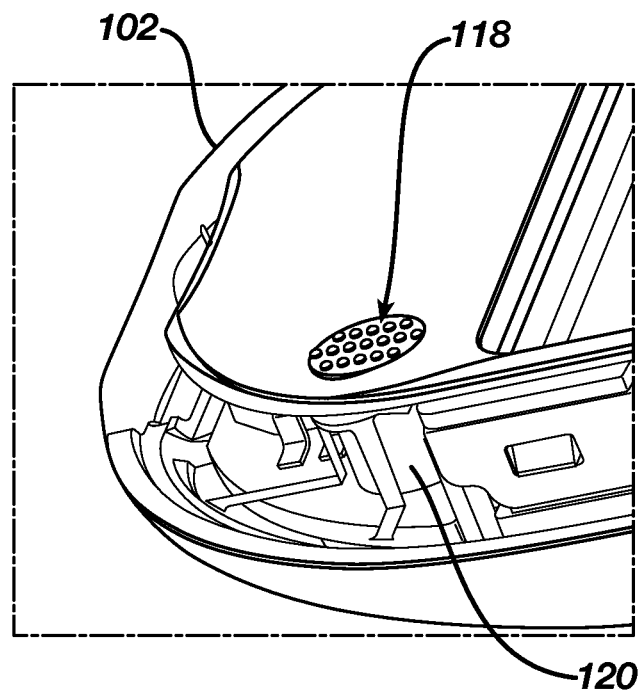
FIG. 7B is a simplified perspective view of a portion of the hand-held test meter of FIG. 1 including an integrated thermal channel thereof.

FIG. 7A is a simplified top view of a portion of the hand-held test meter of FIG. 1 including an integrated thermal channel thereof. FIG. 7B is a simplified perspective view of a portion of the hand-held test meter of FIG. 1 including an integrated thermal channel thereof.

Figure 8:
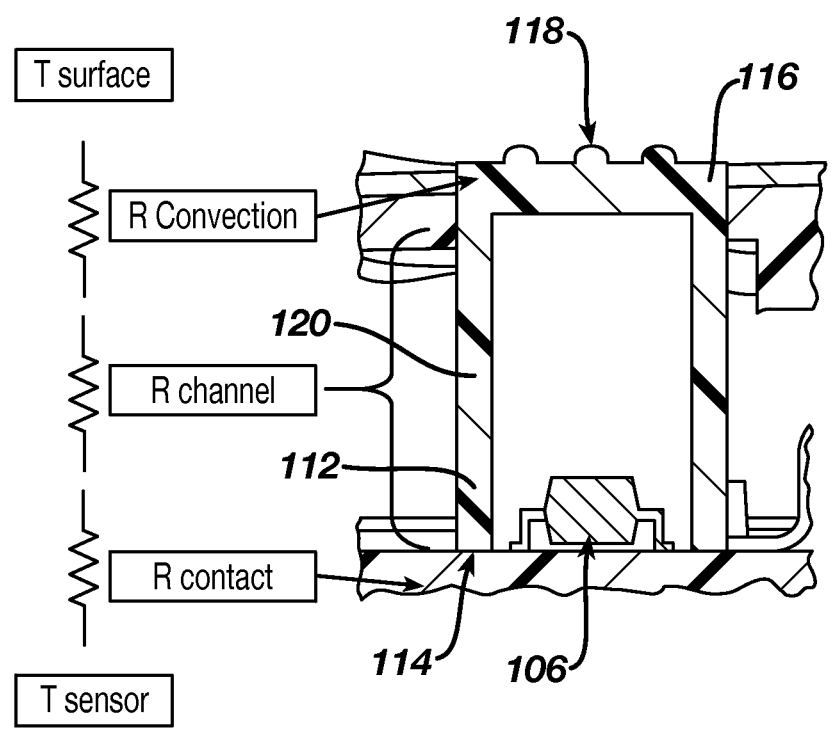
FIG. 8 is a simplified cross-sectional depiction of a portion of the hand-held test meter of FIG. 1 including an integrated thermal channel, an electronic component (i.e., a thermal sensor) disposed on a printed circuit board (PCB) thereof along with an illustrative thermal transfer electrical schematic model.
Figure 9:
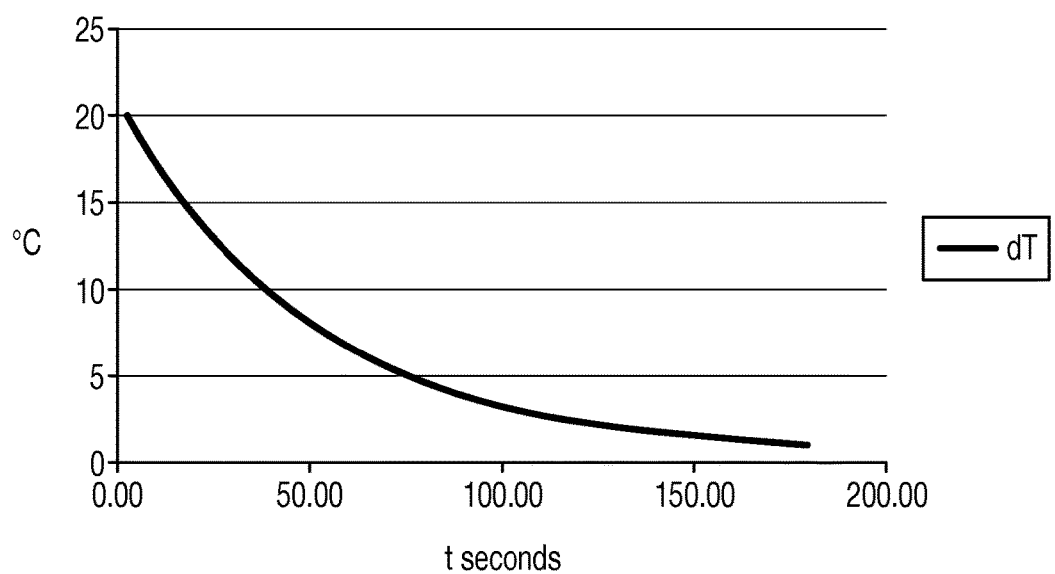
FIG. 9 is a graph of temperature delta (dT) versus time (in seconds) illustrating a beneficial aspect of thermal channels employed in embodiments of the present invention.

FIG. 8 is a simplified cross-sectional depiction of a portion of hand-held test meter 100 including an integrated thermal channel, an electronic component (i.e., a thermal sensor) disposed on a Printed Circuit Board (PCB) thereof along-side of an illustrative thermal transfer electrical schematic model of the cross-sectional depiction. FIG. 9 is a graph of temperature delta (dT) versus time (t, in seconds) illustrating a beneficial aspect of thermal channels employed in embodiments of the present invention.

Referring to FIGS. 1 through 7B, hand-held test meter 100 for the determination of an analyte (i.e., glucose) in a bodily fluid sample (namely, a whole blood sample) includes an electrically and thermally insulating case 102 with an outwardly facing surface 104, a test meter electrical component 106 (namely a temperature sensor) with a thermal contact portion 108 disposed within electrically and thermally insulating case 102, and a thermal channel 110. Hand-held test meter 100 also includes a display 103 and user operable buttons 105. In various FIGS. (such as, for example, FIGS. 2, 6B and 7), side portions of electrically and thermally insulating case 102 are depicted as transparent to expose features and components that would otherwise be hidden from view in the figures. However, the side portions of electrically and thermally insulating case 102 are typically, but not necessarily, opaque.

In the embodiment of hand-held test meter 100, thermal contact portion 108 is configured as solder pads on the surface of printed circuit board 111 (also referred to as PCB 111) with a variety of electrical components, including temperature sensor 106 (also referred to as a thermal sensor), assembled thereon. For clarity of description, the only electrical component assigned a label is temperature sensor 106 Such solder pads are configured to serve as a thermal interface between thermal channel 110 and the electrical component as well as a traditional electrical interface. Employing solder pads as the thermal interface is beneficial in that such solder pads are essentially a direct thermal link to the internal temperature of the temperature sensor. Moreover, employing the solder pads efficiently uses an otherwise existing electrical pathway for the additional and beneficial purpose of efficient heat transfer. One apprised of the present disclosure, one skilled in the art will recognize that the thermal contact can take other suitable forms in addition to solder pads including, but not limited to, plated copper contacts or other copper layers on PCB 111.

Referring to FIG. 3 in particular, thermal channel 110 includes a proximal contact portion 112 with a proximal contact surface 114, a distal contact portion 116 with a distal surface 118 and an essentially cylindrical channel portion 120 connecting proximal contact portion 112 and distal contact portion 116. One apprised of the present disclosure, one skilled in the art will recognize that the shape of thermal channels employed in embodiments of the present invention can be any suitable shape that provides for a suitably efficient thermal transfer. Such shapes include, but are not limited to, suitable regular geometries such as triangles, squares, pentagons, and the like. Moreover, distal contact portion 116 and/or distal surface 118 can be enlarged relative to the remainder of thermal channel 110 having, for example, a mushroom-like (i.e., hemi-spherical) shape. The dimensions of thermal channel 110 (including the cross-sectional area) can be predetermined using any suitable thermal analysis methods based on, for example, the thermal conductivity of the material of the thermal channel, any thermal contact resistances, the amount of heat to be transferred and the time for such heat transfer. The left-hand side of FIG. 8 depicts an illustrative simplified thermal channel electrical schematic model that can be employed to analyze the thermal behavior of a thermal channel.

Thermal channel 110 is integrated with electrically and thermally insulating case 102 such that thermal channel 110 extends through electrically and thermally insulating case 102 from outwardly facing surface 104 to thermal contact portion 108 of test meter electrical component 106 such that proximal contact surface 114 is outside of electrically and thermally insulating case 102 and distal surface 118 is in operable thermal contact with thermal contact portion 108 of the test meter electrical component 106.

Thermal channel 110 is thermally conductive and electrically-insulating and, therefore, directly transfers heat from the ambient environment outside of electrically and thermally insulating case 102 to the thermal contact portion of test meter electrical component 106 in a beneficially timely manner. Thermal channel 110 can have, for example, a thermal conductivity in the range of 1.0 Wm/° K to -20 Wm/° K and an electrical resistivity above 1 M ohm-meter. Electrical component 106 can be, for example, a commercially thermal sensor available as part numbers TMP112 and LM61CIM3 from Texas Instruments, Dallas Tex., USA.

Electrically and thermally insulating case 102 can be formed of any suitable material including, for example, plastic materials. Suitable plastic materials include, for example, polypropylene, polystyrene and polycarbonate, poly(methyl methacrylate) (PMMA), polyoxymethylene (POM), acrylonitrile butadiene styrene (ABS), a glass-reinforced liquid crystal polymer (LCP) and combinations thereof. The plastic material of the electrically-insulating casing is selected such that it is compatible with, for example has operable adhesion with, thermal channel 110.

Electrically and thermally insulating case 102 can have, for example a thermal conductivity of less than 0.1 W/mK.

Thermal channel 110 can be manufactured as either a separately molded component that is clipped or snapped into place or incorporated in the standard plastic casing by means of a co-injection molding process. It can also be mechanically fixed to the PCB by screwing or heat staking. Thermal channel 110 is disposed on an upper surface of hand-held test meter 100 and spaced sufficiently apart from locations where a user may grip hand-held test meter 100 that a potential inadvertent transfer of thermal energy from the user's body to the thermal channel and subsequently to the thermal sensor is minimized, thereby avoiding a deleterious increase in sensed temperature.

Thermal channel 110 can, for example, be a rigid thermoplastic doped with thermally conductive (and electrically insulating) micro-particles and/or/nanoparticles. Examples of suitable micro-particles and nano-particles are those formed of thermally conductive materials including beryllium oxide, aluminum oxide, zinc oxide, aluminum nitride, silicon dioxide, glass, silica, and quartz. Various theories have been developed to explain and predict the thermal characteristics obtained by doping thermally non-conductive materials with thermally-conductive particles. See, for example, Zhang, G (2009), "A Percolation Model of Thermal Conductivity for Filled Polymer Composites," Journal of Composite Materials.

One exemplary, but non-limiting, material that is suitable for a thermal channel is available from Ovation Polymers under the trade name Nemcon H. This material reportedly has an in-plane conductivity of up to 20 W/mK and a through-plane conductivity of up to 3.5 W/mK. Considering the thermal conductivity of standard thermo plastic used in casings for hand-held test meters is in the order of 0.1 W/mK, such a material has a significantly improved heat transfer capability.

Once apprised of the present disclosure, one skilled in the art will recognize that hand-held test meter 100 can be readily configured to operate as a hand-held test meter for the determination of an analyte (such as glucose) in a bodily fluid sample (e.g., a whole blood sample) using a test strip (for example, an electrochemical-based analytical test strip).

The thermal channel employed in embodiments of the present invention can be employed, for example, to (i) transfer heat from the environment to an electrical component of the hand-held test meter or (ii) transfer heat from an electrical component of a hand-held test meter to the environment. An illustrative example of the latter is the transfer of heat (i.e., thermal energy) from a portion of a PCB within the hand-held test meter to the external environment via a thermal channel. The performance of such a heat transfer can be modeled, in a simplified but illustrative manner, as follows.

The applicable PCB portion containing thermal energy is assumed to have a 30 mm diameter and 1 mm thickness. Moreover, the PCB is assumed to consist of copper (with a negligible thermal capacity and FR4 material). The external environment is assumed to be air with e negligible thermal capacity. It also assumed that the distal surface of the thermal channel is at ambient temperature due to forced convention.

The volume of the PCB portion is then calculated as:

r=0.015 h=0.001

Volume=$\pi \cdot r^2 \cdot h$=7.06×10$^{-7}$ ($m^3$)

Assuming the mass of FR4 material is 0.001307 kg, a temperature rise above ambient of 20 C, and an FR4 heat capacity (ignoring the hear capacity of copper) of 600 J kg$^{-1}$K$^{-1}$.

The mass of FR4 material (assuming a density 1850 kgm$^{-3}$)=0.001307 (kg) is: E=c·m·ΔT=15.6J An illustrative thermally conductive plastic energy transfer calculation for the thermal channel is as follows. Assuming the thermal channel is essentially a hollow cylinder of thermally conductive plastic with outer diameter of 6 mm, an inner diameter of 4 mm, and a height of 5 mm, the area of contact to PCB (assuming perfect interface) is:

$A = \pi r_1^2 - \pi r_2^2 = 1.5708 \times 10^{-5}$ $m^2$

Assuming Fourier's law for conductive heat transfer (q):
k=thermal conductivity of plastic (assumed to be 5 W/mK)
s=thickness =0.00
q=k A dT/s5 m and time (t) to transfer energy is:

$$t = \frac{E}{P}$$

Then the successive time to drop 1° C. (noting that the thermal conductivity lowers as the temperature difference drops can be calculated using essentially a piecemeal integration calculation). The assumption here is that the FR4 conducts its heat to the thermal channel perfectly. The resulting temperature difference between the electrical component (at an elevated temperature compared to the environment) is illustrated in FIG. 9.

Figure 10:
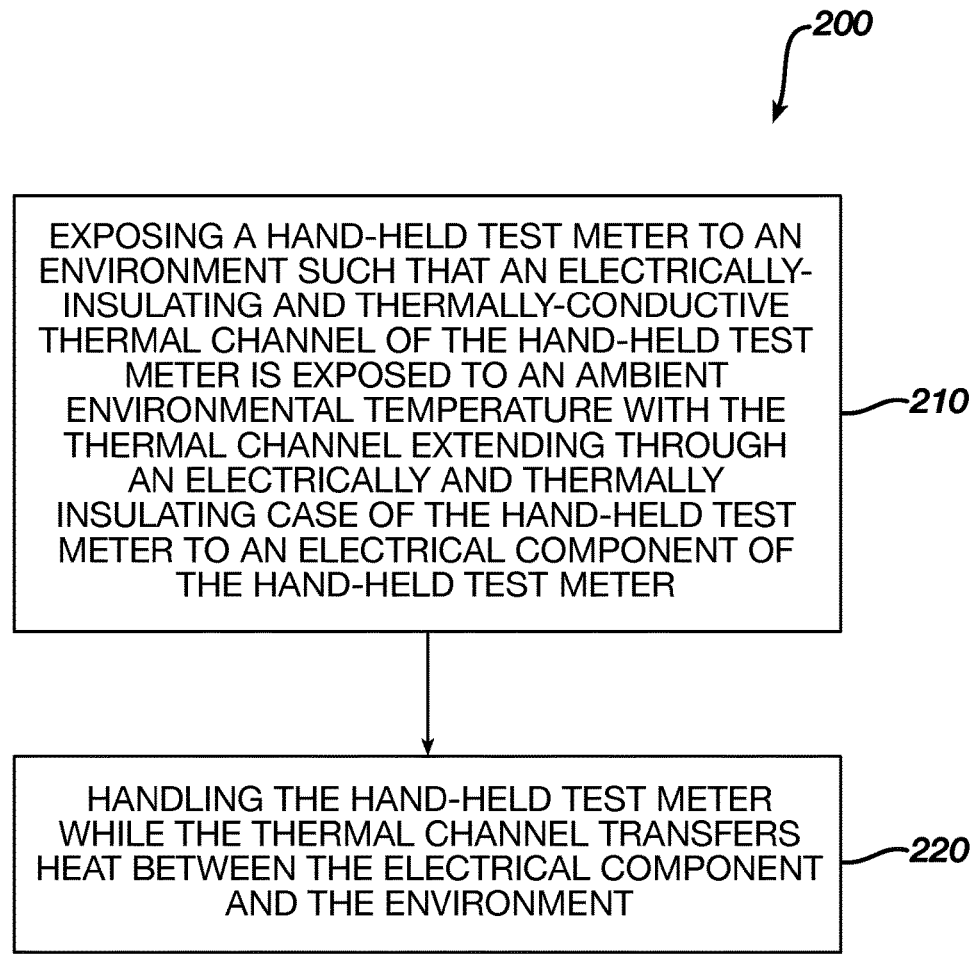
FIG. 10 is a flow diagram depicting stages in a method for employing a hand-held test meter according to an embodiment of the present invention.

FIG. 10 is a flow diagram depicting stages in a method 200 for handling a hand-held test meter (such as hand-held test meter 100 described herein and other hand-held test meters according to the present invention).

Method 200 includes, at step 210 of FIG. 10, exposing a hand-held test meter to an environment such that an electrically-insulating and thermally-conductive thermal channel of the hand-held test meter is exposed to an ambient environmental temperature, the thermal channel being integrated with an electrically and thermally insulating case of the hand-held test meter such that the thermal channel extends through the electrically and thermally insulating case and to a thermal contact portion of a test meter electrical component.

Method 200 also includes handling the hand-held test meter while the thermal channel transfers heat between the test meter electrical component and the environment (see step 220 of FIG. 10).

Once apprised of the present disclosure, one skilled in the art will recognize that method 200 can be readily modified to incorporate any of the techniques, benefits, features and characteristics of hand-held test meters with integrated thermal channels according to embodiments of the present invention and described herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that devices and methods within the scope of these claims and their equivalents be covered thereby.

What is claimed is:

1. A hand-held test meter comprising:
   an electrically and thermally insulating case with:
      an outwardly facing surface;
   at least one test meter electrical component with a thermal contact portion disposed within the electrically-insulating case; and
   at least one thermal channel formed of a rigid thermoplastic material doped with thermally-conductive, electrically-insulating micro-particles or nano-particles, the at least one thermal channel includes:
      a proximal contact portion with a proximal contact surface;
      a distal contact portion with a distal surface, and
      a channel portion connecting the proximal contact portion and the distal contact portion;
   wherein the at least one thermal channel is integrated with the electrically and thermally insulating case such that the thermal channel extends through the electrically and thermally insulating case from the outwardly facing surface and to the thermal contact portion of the test meter electrical component such that the proximal contact surface is outside of the electrically and thermally insulating plastic case and the distal surface is in contact with the thermal contact portion of the test meter electrical component; and
   wherein the thermal channel is thermally conductive and electrically-insulating.

2. The hand-held test meter of claim 1 wherein the hand-held test meter is configured for the determination of an analyte in a bodily fluid sample.

3. The hand-held test meter of claim 2 wherein the analyte is glucose and the bodily fluid sample is a whole blood sample.

4. The hand-held test meter of claim 1 wherein the electrically and thermally insulating case has a thermal conductivity of less than approximately 0.1 W/mK and the thermal channel has a thermal conductivity in the range of approximately 1.0 W/mK to 20 W/mK.

5. The hand-held test meter of claim 1 wherein the electrically and thermally insulating case has a thermal conductivity of approximately 0.1 W/mK and the thermal channel has a thermal conductivity greater than approximately 3.5 W/mK.

6. The hand-held test meter of claim 1 wherein the electrically and thermally insulating case is formed of a plastic material.

7. The hand-held test meter of claim 1 wherein the channel portion of the thermal channel has an essentially cylindrical configuration.

8. The hand-held test meter of claim 1 wherein the channel portion has a prismatic configuration.

9. The hand-held test meter of claim 1 wherein the distal contact portion of the thermal channel has a textured surface.

10. The hand-held test meter of claim 1 wherein the at least one micro-particles and nano-particles are formed of at least one of beryllium oxide, aluminum oxide, zinc oxide, aluminum nitride, and silicon dioxide.

11. The hand-held test meter of claim 1 wherein the electrically and thermally insulating case is formed of a plastic material.

12. The hand-held test meter of claim 1 wherein the at least one test meter electrical component is a micro-controller.

13. The hand-held test meter of claim 1 further including a printed circuit board (PCB) disposed within the electrically and thermally insulating case and
   wherein the at least one electrical component is mounted on the PCB, and
   wherein the thermal contact surface is at least one of a solder pad and a copper layer in contact with the electrical component.

* * * * *